United States Patent [19]

Shapira

[11] Patent Number: 5,460,602

[45] Date of Patent: * Oct. 24, 1995

[54] SMOKE EVACUATOR FOR SMOKE GENERATING DEVICES

[76] Inventor: Nadiv Shapira, 4745 Ogletown-Stanton Rd., Newark, Del. 19713

[*] Notice: The portion of the term of this patent subsequent to Mar. 9, 2010 has been disclaimed.

[21] Appl. No.: 27,825

[22] Filed: Mar. 8, 1993

Related U.S. Application Data

[63] Continuation-in-part of Ser. No. 678,169, Mar. 28, 1991, Pat. No. 5,192,267, which is a continuation of Ser. No. 300,180, Jan. 23, 1989.

[51] Int. Cl.$^6$ ............................................. A61B 17/20
[52] U.S. Cl. ........................... 604/22; 604/35; 604/119; 606/39; 606/45
[58] Field of Search .................... 604/22, 73, 35, 604/118, 119, 317, 902; 606/13, 27–29, 39–42, 45, 49; 15/415.1; 55/456, 457; 137/808–812; 138/37, 39, 42; 366/336; 406/152

[56] References Cited

U.S. PATENT DOCUMENTS

| | | |
|---|---|---|
| 818,891 | 4/1906 | Jones et al. . |
| 1,086,763 | 2/1914 | Goersch . |
| 2,086,496 | 8/1937 | Geldhof . |
| 2,808,833 | 10/1957 | August . |
| 2,888,928 | 6/1959 | Seiger . |
| 3,394,533 | 7/1968 | Li et al. . |
| 3,495,385 | 2/1970 | Glass . |
| 3,902,494 | 9/1975 | Haberlen et al. . |
| 3,906,955 | 9/1975 | Roberts . |
| 3,964,484 | 6/1976 | Reynolds et al. .......... 604/902 |
| 3,964,484 | 6/1976 | Reynolds et al. . |
| 3,974,833 | 8/1976 | Durden, III . |
| 3,982,541 | 9/1976 | L'Esperance, Jr. . |
| 4,002,170 | 1/1977 | Hansen et al. ............ 604/902 |
| 4,074,718 | 2/1978 | Morrison, Jr. . |
| 4,112,950 | 9/1978 | Pike . |
| 4,170,234 | 11/1979 | Graham . |
| 4,362,160 | 12/1982 | Hiltebrandt . |
| 4,562,838 | 1/1986 | Walker .......................... 604/35 |
| 4,668,981 | 5/1987 | Egger . |
| 4,683,884 | 8/1987 | Hatfield et al. . |
| 4,688,569 | 8/1987 | Rabinowitz . |
| 4,719,914 | 1/1988 | Johnson ........................ 604/35 |
| 4,888,003 | 12/1989 | Johnson et al. ............. 604/119 |
| 4,963,134 | 10/1990 | Backscheider et al. . |
| 4,986,827 | 1/1991 | Akkas et al. . |
| 5,047,072 | 9/1991 | Wertz et al. . |
| 5,181,916 | 1/1993 | Reynolds et al. . |

*Primary Examiner*—John D. Yasko
*Assistant Examiner*—Bryan L. Tsosie
*Attorney, Agent, or Firm*—Lackenbach Siegel Marzullo Aronson & Greenspan

[57] ABSTRACT

A smoke removing device adaptable to many fields but preferably used with electrosurgical devices consisting of a hollow tube for evacuating the smoke, a tubular housing including vortex means for creating a vortex at an entrance end of the tubular housing, and an exit end of the tubular housing adapted to be connected to one end of the hollow tube, another end of the hollow tube being adapted to be connected to a suction means for creating suction to remove the smoke form the air near the smoke generator. A vacuum booster is provided for optionally enhancing the suction and vortex created at the entrance of the tubular housing.

10 Claims, 7 Drawing Sheets

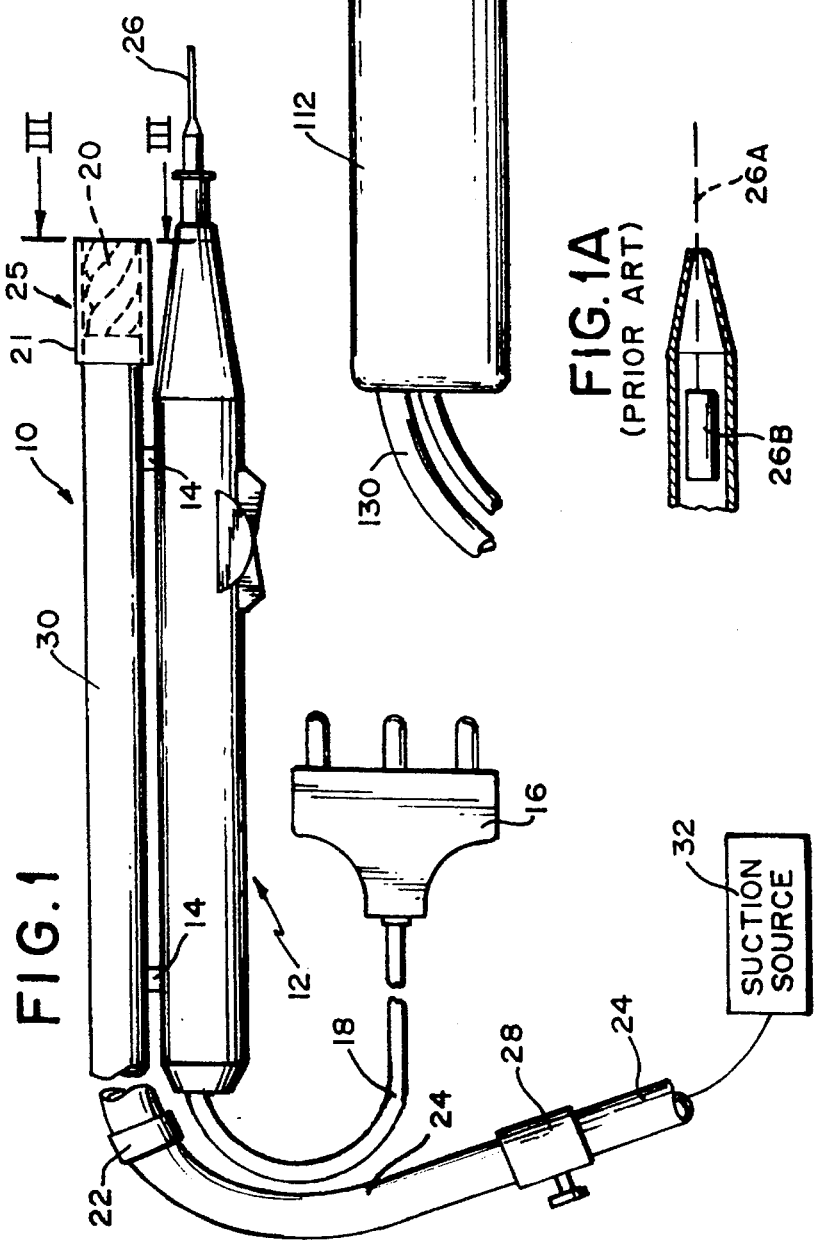
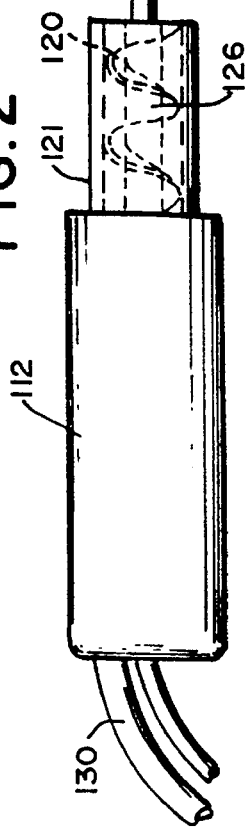
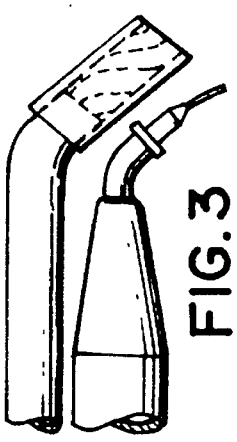
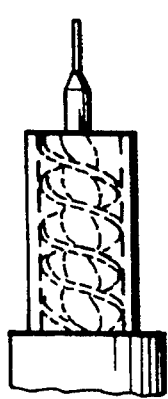
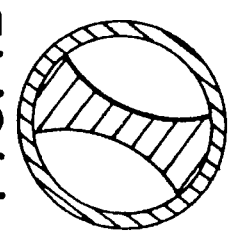
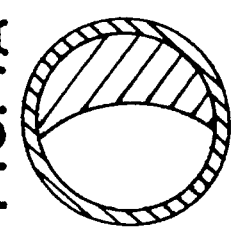

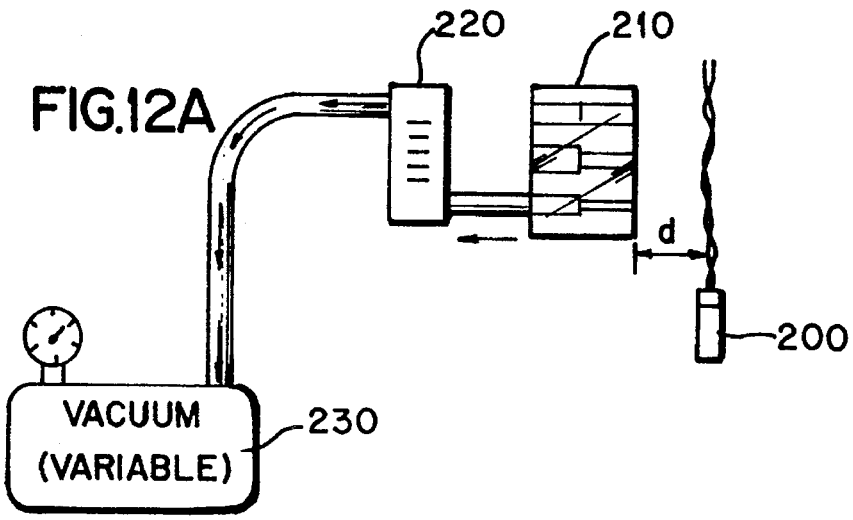
FIG.12A
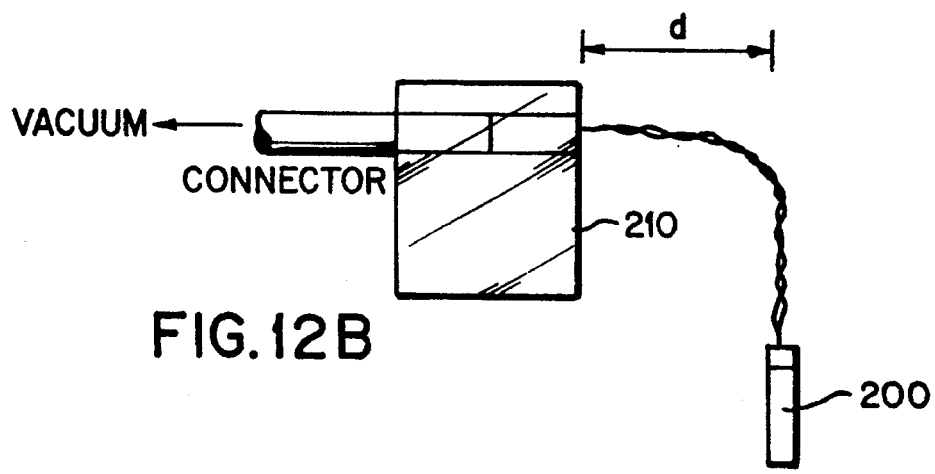
FIG.12B
FIG.13
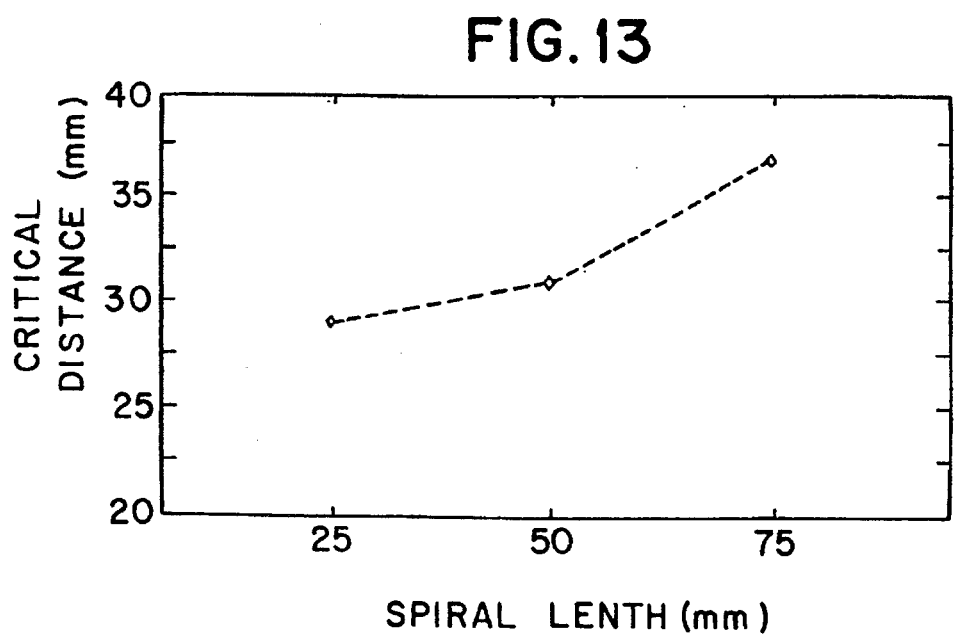

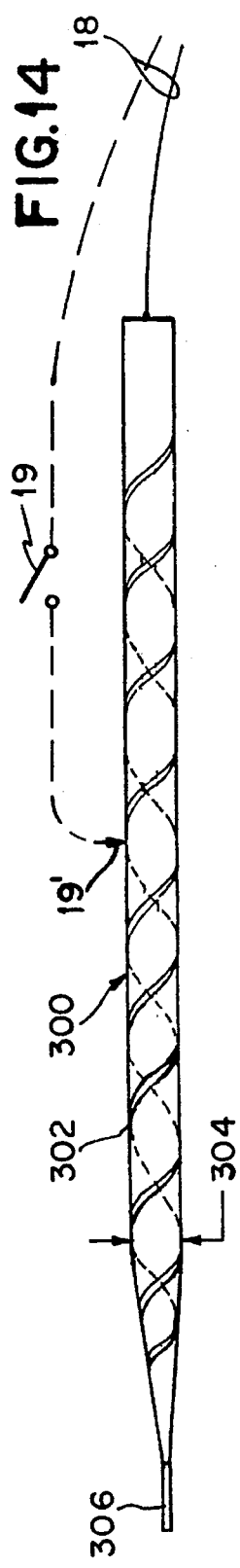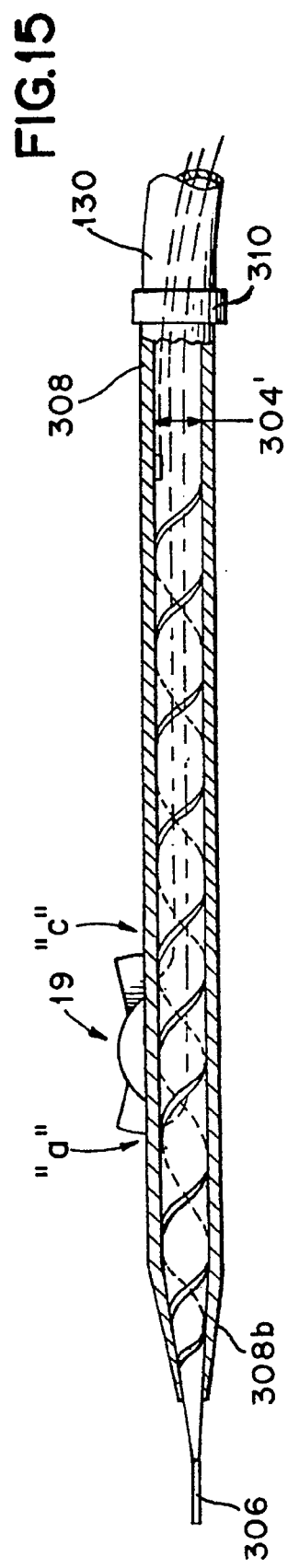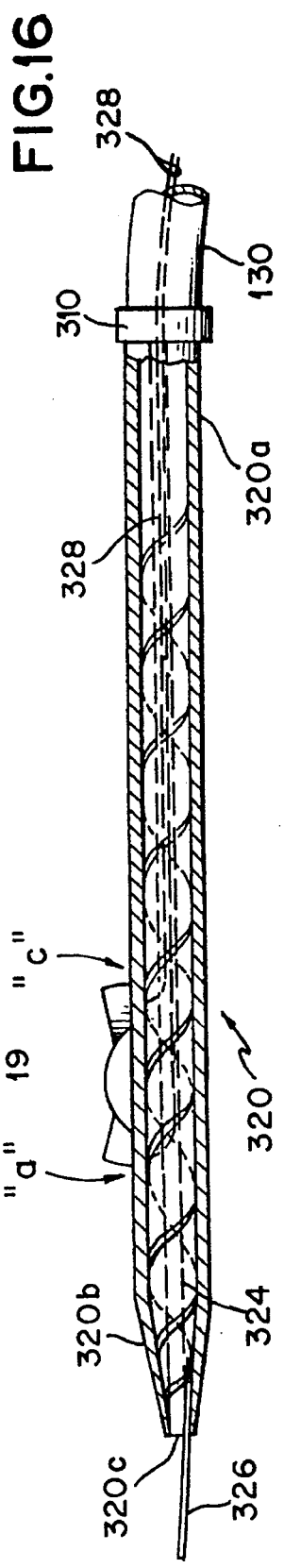

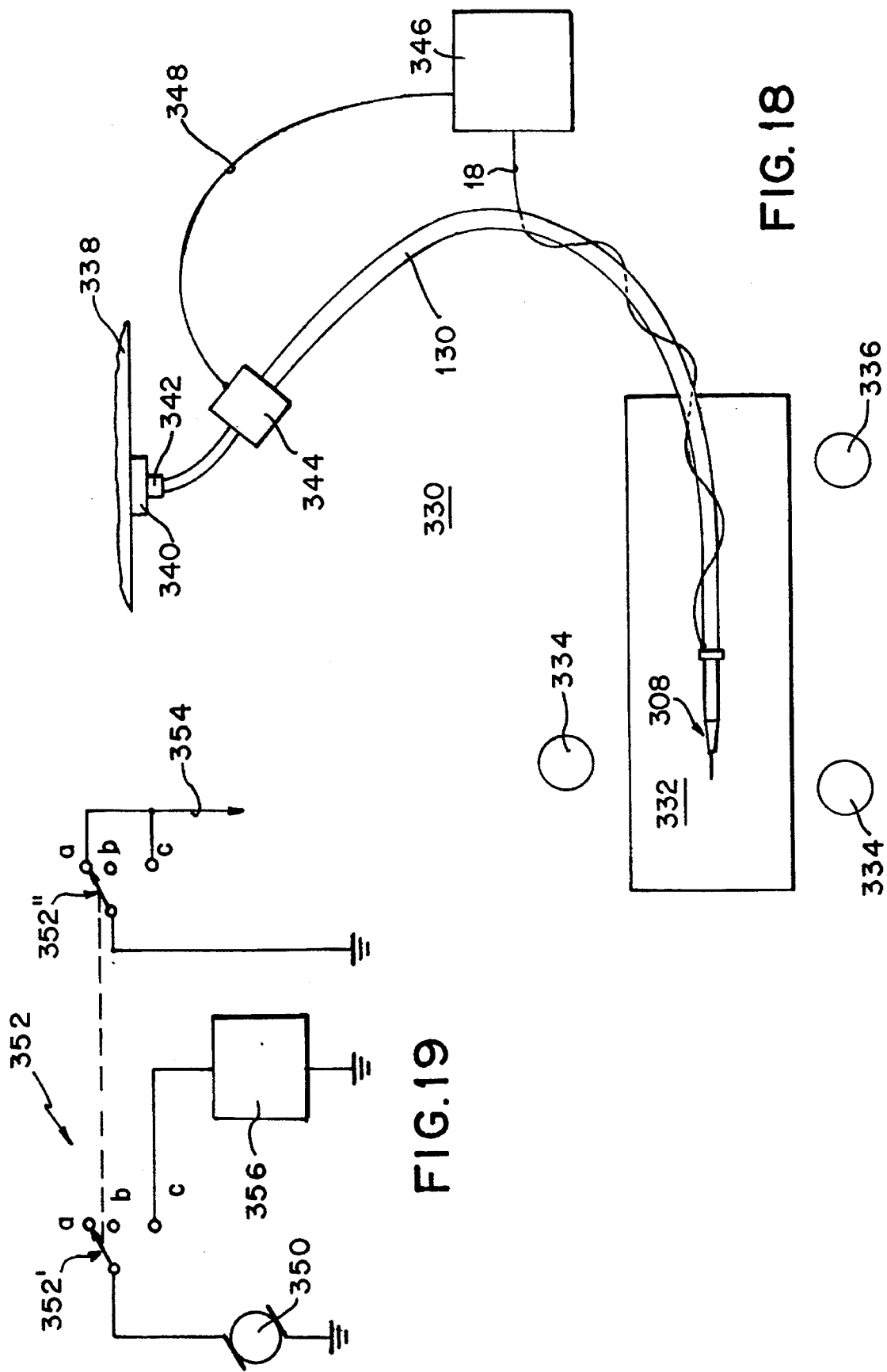

SMOKE EVACUATOR FOR SMOKE GENERATING DEVICES

CROSS REFERENCE TO RELATED APPLICATIONS

This is a continuation-in-part (C.I.P.) application of application Ser. No. 07/678,169 filed on Mar. 28, 1991 now U.S. Pat. No. 5,192,267, which is a continuation of application Ser. No. 27/300,180, filed on Jan. 23, 1989.

FIELD OF THE INVENTION

The present invention relates to improvements in smoke removal and, more particularly, to a smoke evacuating device for use with surgical electrocautery devices.

BACKGROUND OF THE INVENTION

Hand-held electrosurgical instruments, such as electrocautery or laser surgical devices are used in many branches of surgery for the bloodless cutting of tissue, and for the cauterizing of vessels to stop bleeding. During surgical use the localized heat generated by the electrical discharge causes large amounts of noxious smoke to be produced. This high temperature smoke rises rapidly from the point of the cautery instrument. Various studies have indicated that the smoke may contain carcinogenic elements, potentially harmful to the operating room staff. In addition the smoke is sometimes produced in such volume that the surgeon's view of the operative field is obscured. In other circumstances, the anatomy causes the smoke to be trapped. Such a case is the dissection of the left internal mammary artery for subsequent coronary artery bypass grafting. The internal mammary artery lies beneath the left rib cage, several centimeters to the left of the midline incision. The smoke generated during the dissection of the vessel tends to collect in the chest cavity. It is therefore desirable to provide a smoke collection system to remove the nuisance, smell and potential hazard of the smoke. At the same time, the collection system should not unduly interfere with the surgeon's field of view of the tissues being cut, nor can the device interfere with the use of the electrosurgical instrument.

A number of electrosurgical devices are available which do not include any suction capabilities for removing smoke from the operating area. For example, U.S. Pat. Nos. 4,074,718; 4,112,950; 4,170,234; 4,688,569; and 4,986,827. Additionally, other U.S. patents disclose devices which do include suction capabilities. For example, U.S. Pat. Nos. 2,275,167; 3,266,492; and 3,906,955 disclose such devices. These devices include a tube connected to a source of vacuum which runs parallel to the cautery blade. U.S. Pat. No. 4,362,160 discloses an endoscope which includes passages for feeding in and drawing off scavenging or flushing liquid which extends longitudinally behind the cutting or coagulating loop.

It is further known to attach suction means to electrocoagulating devices, as shown in U.S. Pat. Nos. 2,808,833; 2,888,928; and 4,686,981. However, U.S. Pat. Nos. 2,808,833 and 4,686,981 include suction means for the express purpose of withdrawing excess blood prior to coagulating the remaining blood. U.S. Pat. No. 2,888,928 discloses a coagulating surgical instrument which includes a plurality of openings disposed at right angles with respect to the longitudinal axis of the cautery tip. Therefore, the suction operates to clear an area which is not immediately adjacent to the coagulating instrument. Other patents, such as U.S. Pat. Nos. 3,974,833; 4,562,838; 4,683,884; and 4,719,914, disclose an electrosurgical instrument with a smoke dissipating means which is concentric with the cutting blade, or in the case of U.S. Pat. No. 3,982,541, concentric with the laser beam passage. U.S. Pat. No. 5,181,916 discloses a surgical probe and smoke eliminator that incorporates either an annular suction port for laminar air flow intake or a series of circumferentially arranged nozzle orifices configured to create a vortex in the immediate vicinity upstream of distal end of the probe. The nozzle orifices are angularly arranged, as opposed to the longitudinal arrangement of the annular suction port, to induce rotary motion of the smoke in the space around the probe target area.

The processes using electrosurgical devices such as cauterization, laser surgery, and coagulation, are very different procedures. Cauterization involves the use of a hot iron, an electric current or a caustic substance to destroy tissue. Laser surgery involves the use of a precisely controlled laser beam to cut or destroy tissue. Coagulation deals with the process of blood clot formation.

Although the various patents dealing with these devices disclose the general principle of providing a suction passage to the cutting or business end of the device, their particular constructions create difficulties in their use. Namely, they are limited by their structure to removing smoke which is close to the inlet of the suction means. In particular, the structures are such that the vacuum input tube remains very close to the tip of the electrocautery blade generating the smoke. Thus, the surgical field may be obscured from view either by smoke, or by the vacuum input tube itself. In those patents in which the vacuum input tube is far from the cutting surface, the suction is likely to be ineffective in removing all smoke form the surgical field because of the distance between the vacuum input tube and the cutting surface.

Further, in a number of these prior art devices, it is not possible to effectively remove the smoke because the suction tube or passage becomes clogged with blood. It is of the utmost importance that smoke created by the electrocautery, laser surgical or coagulation device be efficiently removed from the surgical field. Smoke created by these devices is suspected of being carcinogenic and mutagenic. Thus, it is necessary to remove the smoke from the surgical field to insure the safety of the surgery team. U.S. Pat. No. 4,963,134 discloses a laser surgery plume evacuator with an aspirator. The evacuator is not connected to a standard wall vacuum receptacle in an operating room (OR). Instead, the evacuator is connected to a self-contained portable unit that includes a source of vacuum. The evacuator includes an intake nozzle which sucks in the plume but which does not form part of the surgical probe. Therefore, the nozzle must be separately handled and may interfere with the surgeon's manipulations of the probe. Also, instead of exhausting the plume through the OR standard wall vacuum, it must be purified and filtered and again exhausted into the OR environment. Therefore, unless purification is complete, the offensive or contaminating substances are re-released into the OR. A similar stand-alone laser plume evacuation system is disclosed in U.S. Pat. No. 5,047,072. Both aforementioned patents disclose control over the vacuum source so that the amount of suction at the suction wand can be modified.

The smoke created by these devices must also be efficiently removed from the surgical field because it obscures the surgeon's view of the surgical field and is an irritant to the surgeon's eyes. The smoke is odorous and interferes with the surgeon's concentration during the operation.

U.S. Pat. Nos. 818,891; 3,394,533; and 3,495,385 disclose devices that include helical shaped members through which fluids flow, although none of these patents discuss the use of a helical element for smoke removal.

SUMMARY OF THE INVENTION

The present invention improves smoke removability by providing a vortex creating portion in the form of a helical member at the intake of the smoke removing tube. Webster's New Collegiate Dictionary defines a vortex as "a mass of fluid having a whirling or circular motion tending to form a cavity or vacuum in the center of the circle, and to draw toward this cavity or vacuum bodies subject to its action." In the present invention, the creation of the vortex suction causes smoke to be pulled in from a wider area, from a greater distance, and at a quicker rate than that available using an unaltered smoke removing tube.

It is therefore one of the objects of the present invention to provide an improved smoke removable device that can be used during electrosurgery to remove smoke created during an operation.

It is a further object of this invention to provide an improved smoke removal device which is in combination with an electrosurgical device.

It is a further object of this invention to provide an improved smoke removal device which efficiently removes smoke from the surgical field.

It is a further object of this invention to provide an improved smoke removal device which efficiently removes smoke from the surgical field so that the surgeon's concentration is not interfered with during the surgical procedure.

It is a further object of this invention to provide a smoke removing device which uses a vortex in a tube to create a whirlpool motion outside the tube resulting in increased amounts of smoke being sucked into the tube.

It is a further object of this invention to provide a smoke removing device by which smoke is removed more effectively then the prior art devices when the tube inlet is farther away from the cutting surface.

It is a further object of this invention to use the smoke removal device of the present invention to remove smoke, or other noxious atmospheres, as required in other fields including, but not limited to, smoke removal necessary for restaurants, fire fighting, and various other industrial applications.

According to the present invention, a device for removing smoke from the air near a smoke generator is provided comprising a hollow tube for evacuating the smoke, a tubular housing including vortex means for creating a vortex at an entrance end of the tubular housing, and an exit end of the tubular housing adapted to be connected to one end of the hollow tube, another end of the hollow tube being adapted to be connected to a first suction means for creating suction to remove the smoke from the air near the smoke generator. Second suction means selectively increases the suction and vortex at the entrance to the tubular housing.

The smoke generator may be an electrosurgical device.

An electrosurgical device is provided which includes a cutting and cauterizing means in electrical communication with an external power source, a tube having a vortex end and adapted to be connected to a vacuum generator for removing smoke created with the cutting and cauterizing means from an adjacent immediate area, and means for turning on and off the vacuum suction device located at a distance spaced from the cutting and cauterizing end of the device.

Still other objects, features and attendant advantages of the present invention will become apparent to those skilled in the art from a reading of the following detailed description of the embodiments constructed in accordance therewith, taken in conjunction with the accompanying drawings.

BRIEF DESCRIPTION OF THE DRAWINGS

These and other objects of the present invention will become clearer when considered with the drawings and the detailed description of the preferred embodiments, shown by way of example in the drawings in which:

FIG. 1 is a plan view of an electrosurgical device including the smoke removal device according to a first embodiment of the present invention;

FIG. 1a is a plan view of a prior art electrosurgical laser tipped cutting instrument as an example of the laser type hand-held prior art electrosurgical instruments listed in the "BACKGROUND OF THE INVENTION" section above.

FIG. 2 is a plan view of an electrosurgical device including the smoke removal device according to a second embodiment of the present invention;

FIG. 3 is a plan view of a third embodiment of the present invention;

FIGS. 4A, 4B, and 4C are a set of cross-sectional views of different vortex creating tubes which can be used in accordance with the present invention, taken along the line III—III of FIG. 1;

FIG. 5 is a plan view of a fourth embodiment of the present invention in which the tip of the electrocautery device and the vortex tip of the suction tube are roundly curved.;

FIG. 12A is another schematic view showing a distance "d" test conducted with the three orifice blocks shown in FIG. 11;

FIG. 12B is a detailed schematic view of a single orifice, distance "d" and a vacuum connection of the apparatus of FIG. 12A;

FIG. 13 is a plot of critical distance against a spiral length where the turn density is one turn per 25 millimeters;

FIG. 14 is a side elevational view of an externally fluted central electrode in accordance with another embodiment of the invention;

FIG. 15 is a longitudinal section of a cylindrical probe housing incorporating the central electrode shown in FIG. 14;

FIG. 16 is a diagramatic representation, in side elevation of an internally fluted cylindrical probe housing in accordance with a further embodiment of the invention;

FIG. 17 is an end view of the probe shown in FIG. 16;

FIG. 18 is a schematic of a system set-up using the probes of the present invention in a typical operating room (OR) arrangement and using a vacuum booster to selectively enhance the evacuation capabilities of the surgical probe; and FIG. 19 is an electrical schematic that can be used with the arrangement of FIG. 18.

DETAILED DESCRIPTION OF THE PREFERRED EMBODIMENTS

Figure 6:
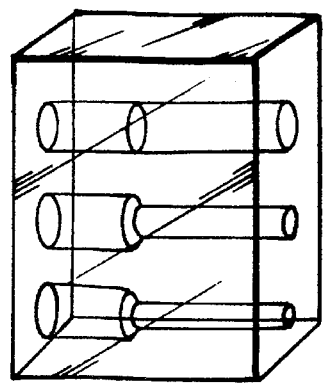
FIG. 6 is a block diagram of three orifice diameters used to demonstrate the efficiency of the vortex tube according to the present invention.

FIG. 1 schematically shows a typical electrosurgical cutting or coagulating device 12. One embodiment of the present invention is one in which the smoke remover device 10 is removably attached to device 12. The remover 10 can be attached to the electrosurgical device using various types of attaching means 14 such as mounting brackets or the like. The electrosurgical device 12 receives power from a power source (not shown) through plug 16, which can be adapted to fit various power sources, and then through electrical cord 18 to the device 12.

The smoke remover 10 consists of a hollow tubular base or housing 30 and a vortex creating member 25 attached to the base B0. Tube 21 and base 30 may be constructed of plastic. The vortex creating member 25 includes a twisted piece of material 20, for example, stainless steel fit within the tube 21. As an example, a section of drill bit wedged within an appropriately sized tube will provide the desired effect. the vortex creating member 25 is removably inserted onto the end of base 30.

A set of interchangeable tips including the straight vortex tip shown in the present embodiment in FIG. 1 may be provided. The various tips are interchangeable as the situation requires to enable the operating surgeon to clear away the maximum amount of smoke. Some of the various tips that could be used include the straight vortex tip 20 of the embodiment shown in FIG. 1, a sharply or roundly curved vortex tip such as shown in FIG. 5, and various other tips. Additionally, various tips may be provided in which the twisted material 20 is of different lengths.

The smoke remover 10 is attached at attaching joint 22 to a vacuum hose 24 which is attached to a suction source 32 shown schematically on Fig. i at the opposite end of hose 24.

FIG. 1A shows a prior art laser tipped cutting instrument as an example of the laser type hand-held prior art electrosurgical instruments listed in the "BACKGROUND OF THE INVENTION" section above.

This prior art device is shown having a laser beam 26A and a laser source 26B which function to permit bloodless cutting of tissues in an equivalent manner to prior art electrocautery devices also listed with such prior art hand-held electrosurgical instruments.

An alternative embodiment of the present invention is shown in FIGS. 2 and 3. In these embodiments the vortex tip 120 concentrically surrounds the base 126 of the cutting blade 26. The vortex tip 120 can be either removably or permanently attached to the electrosurgical device 112. If the tip 120 is removable then it may be part of a set of interchangeable tips which can be used as the situation requires. A tube 130 is shown coming out of the back of the electrosurgical device 112 to carry the removed smoke to hose 24, which meets tube 130 at intersection joint 22 (not shown). Of course, the tube 130 could be eliminated with the hose 24 connecting directly to the smoke removal device 120 or the back of the electrosurgical device 112.

FIG. 4 shows cut-away cross-sections of three different vortex creating members, along the line III—III of FIG. 1, which could be used in the present invention. The member may be formed in a variety of different shapes, length, and sizes. For example, the piece 20 within the tip may be one-quarter, one-half or one inch long. Additionally, a different number of vanes, fins or blades may be provided in different tips. The member may be either a single or a double helix. For example, FIG. 4A has a single vortex creating opening and would be relatively easy and inexpensive to manufacture. FIGS. 4B and 4C includes two and three vanes, for creating two and three vortex creating openings, respectively and are more complicated and would thus be more expensive to manufacture. FIGS. 2 and 3 illustrate different helical configurations for the vortex member. Other variations of vortex creating members can be easily created and all are intended to be included in the present invention.

The smoke remover 10 system works in the following manner. As the heated cutting blade or electrode 26 of the electrosurgical device 12 makes contact with the patient, smoke is produced from the burning tissue. When the vortex tip 20 is attached to the smoke remover 10, the pressure differential created by the vortex causes increased circulation of the air and smoke just outside of the vortex. Because of the funnel or whirlpool effect created by the pressure differential, smoke can be sucked to the openings from between the vortex creating member and the inside of the tube in from a wider area, from a greater distance, and at a quicker rate.

In fact, the suction of the device 10 is continuous. The suction can be applied even when the blade 26 is not cauterizing. therefore, a negative pressure exists around the blade prior to generation of any smoke and the smoke is never given an opportunity to accumulate at the point of surgery.

Depending on the circumstances of the surgery involved, different vortex tips could be selected to maximize the benefits available using the vortex tip according to the present invention. In situations where the smoke is dissipating over a wider area, the straight vortex tip may provide the most benefit. However, in situations where the smoke is dissipating very slowly over a small area, a venturi vortex tip having a tapered end may be the most efficient choice. In situations where the cutting tip 26 is bent at an angle, the most efficient smoke removing tip might be the bent vortex tip. Additionally, the surgeon could also change the tips for obtaining a vortex having a different strength depending on the length of the helical member. Since the surgeon can easily change tips on the smoke remover, the surgeon will quickly become familiar with which tip is most effective for each situation incurred.

The on-off switch for the electrocautery device is shown at 19 in FIG. 1. This is separate from the on-off for the suction.

The suction for the smoke remover 10 can be turned on using various types of vanes such as vane 28 on the hose 24. the valve 28 is preferably placed on the hose 24 a few feet away from the smoke remover 10 so that the physician can ask a nurse or another member of the support staff to turn the suction on and off, thus keeping his free hand available for other purposes. The valve 28 could just as easily be placed on the smoke remover itself near the cutting edge although it is less desirable for the aforementioned reason. The presence of the valve allows the surgeon to request that the suction be turned off when it is not required in order to eliminate the noise created by the suction source.

The system according to the embodiments shown in FIGS. 2 and 3 is operated in the same manner as the first embodiment with the only difference being that smoke can be removed immediately after it forms since the smoke remover 120 is so close to the source of the smoke.

A number of tests were carried out in order to determine the efficacy of different devices to clear smoke from an operating area.

TEST 1

In a first experiment, smoke was generated using a regular Bovie machine, coagulation set at 100. In the first test, smoke was generated from a blood clot, in the second test, from a small piece of adipose tissue. In both cases the tissue was placed on a regular grounding pad. While smoke was generated, a regular operating room suction device was held with the other hand, and its position was changed in relation to the electrocautery tip (i.e. above or below the tip). In addition, the suction was moved closer and further away from the source of the smoke. Five different tips were attached to the suction:

(1) A regular ¼" tube.

(2) A narrowed tip.

(3) A ¼" tube into which a piece of approximately ½" long of a ¼" drill bit was snugly inserted.

(4) Similar to #3, but with a 1" piece of drill bit.

(5) A mold made of acrylic on a ¼" drill, 1 and ¼" long.

The second tip was designed to created a bernouli effect. The last three tips were designed to generate a vortex suction.

Although a precise quantitative measurement of the smoke clearance could not be done, an assessment of the clearance and the relative effectiveness of each tip could be accomplished. Testing of each tip was repeated about 10 times and the impressions were consistent. The most effective clearance was accomplished with tip #4, tips #3 and #5 were about the same, and tips #1 and #2 were the least effective. The effectiveness was manifested by the wider area of smoke clearing and by the degree of completeness of clearing. Positioning of the suction tip below the pencil did not detract significantly from its function. At times, two streams of smoke could be seen entering the suction tip.

TEST 2

A second experiment was carried out in order to substantiate the previous observation that the #4 vortex tip was superior to the other tips. This tip (¼" tubing into which a 1" long portion of a ¼" drill bit was inserted), was compared to a regular ¼" tubing. In this experiment, a piece of beef fat was used, 5×5×10 cm, utilizing again a regular Bovie and suction system. Two method for assessment of the efficacy of smoke clearance were used, each repeated 10 times.

The first experiment was done while the Bovie pencil was held straight up, and the suction tip perpendicular to the pencil, 1.5" above the pencil tip. In this position, the generated smoke climbed as a column along the pencil. When the suction tip was held very close to the pencil, there was a very efficient smoke clearance. As a matter of fact, the smoke could be clearly seen to divert abruptly from the pencil in a right angle towards, and opposite from, the suction tip. As the suction tip was slowly moved away from the pencil, the column of smoke initially continued to be cleared in a similar fashion, until a certain distance, in which part of the smoke was not cleared any more and rose upwardly. This distance was always longer when the vortex tip was employed, by approximately 30 to 40%, when compared to the clearance distance of the non-vortex tip. The distance was dependent on the amount of smoke generated. When high quantities of smoke were generated, the suction tip had to be held relatively closer in order to achieve a complete clearance, and visa versa. Yet, for any amount of smoke, the vortex tip was able to clear the smoke from a longer distance.

In the second set of experiments, the diameter of the area from which the smoke was cleared was assessed. When the Bovie pencil tip was brought from the side rather than from above, the smoke was generated in all directions, and was spreading like a ball. At times, smoke was even coming out from areas not in direct contact with the Bovie tip. Comparison of the suction tips was preformed by moving them towards and away from the Bovie tip where the smoke was generated. When the non-vortex suction tip was used, the smoke "ball" was very large, and the suction tip had to be held fairly close to the Bovie tip in order to clear all the smoke. In contrast, the vortex tip could be held at a distance approximately twice as long, and still cleared the smoke very effectively. The smoke could be seen spreading like a ball, at times 5–7 cm in diameter, and converge back towards the suction tip.

From these experiments, it can be seen that the vortex suction effects the air surrounding the tip in both distance and diameter. Thus, vortex suction is capable of creating a more effective suction by the same vacuum source.

TEST 3

A third test was conducted to further demonstrate the efficiency of the vortex tube.

The objective of this experiment was to determine the smoke removal efficiency for the following tip configurations:

(a) determine the efficiency, with and without a vortex inducer in the tip; and, (b) vary the diameter of the proposed vacuum cautery orifice.

In summary, it was demonstrated that an orifice with a increased diameter and a vortex inducing insert showed significantly greater smoke removal. Using a vortex enabled placement of the orifice approximately 50% further away from the smoke source as compared to an orifice without the vortex and without reducing the efficiency of smoke removal.

In order to carry out the experiment, three orifice diameters were machined into a block of clear acrylic to a depth of 25.4 mm( 1.0 inches—see FIG. 6). The diameters were 6.35 mm (¼"), 4.76 mm (³⁄₁₆"), and 2.38 mm (³⁄₃₂"). The corresponding drill bit sizes were cut to a length of 25 mm and inserted into the block when measurements were needed "with vortex". The drills acted to induce spiral air flow. A ¼" I.D. hole on the distal side of the acrylic block served to connect the vacuum source with the test orifice. The sides of the orifice tips were at sharp right angles. It was estimated that the drills blocked approximately 40% of the orifice area.

The 6.35 mm (¼") maximum size orifice was chosen because it was equal to the vacuum hose I.D. used in the operating room. Any larger diameter would decrease the vacuum efficiency by dissipating the air flow lines from the orifice.

Figure 7A:
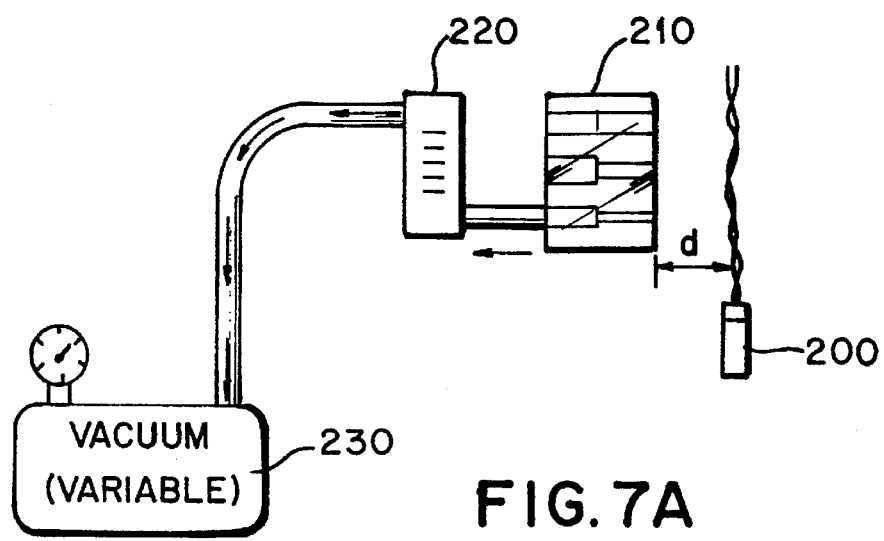
FIG. 7A illustrates the circuit used to measure the efficiency of the vortex tube.

The circuit was set up per FIG. 7a. A vacuum was drawn through 6.35 mm (¼") tubing at a regulated 25 liters/minute gas flow rate. The distal end of the tubing was attached to the orifice of interest and vacuum flow initiated. Each orifice was tested without the drill first, then with the drill.

The smoke source (filtered cigarettes) was placed 6 cm inferior to the orifice and moved either towards or away from the vacuum. If no vacuum was applied, the smoke rose in a concentrated stream for approximately 10–12 cm and then progressively dissipated. Data was taken in both directions. Care was taken to avoid any interfering movement of air. A total of five samples were recorded for each parameter.

Figure 7B:
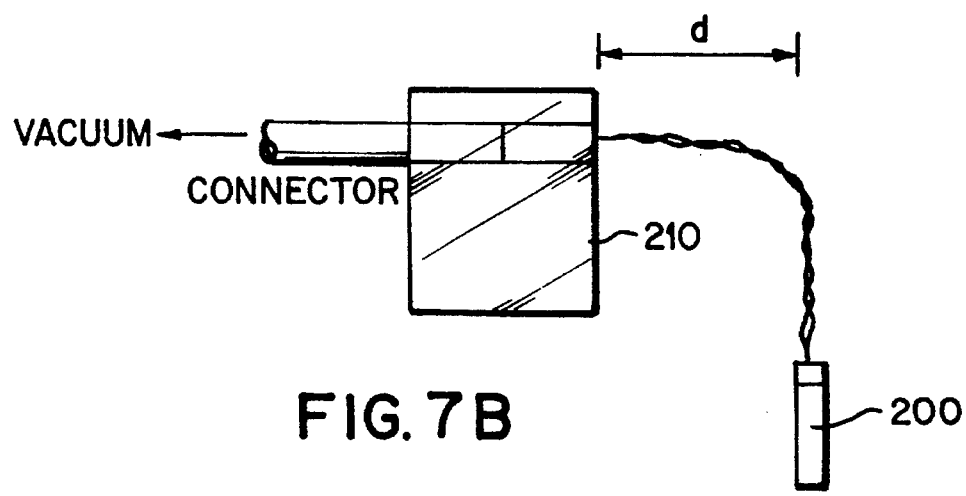
FIG. 7B illustrates the critical distance measured using the vortex tube.

The "critical distance" was defined as the distance "d"(in mm) at which the entire (100%) smoke flow curved towards the vacuum source and was drawn into the vacuum orifice at an obvious right angle to the non-vacuum rising flow (see FIG. 7b). The accuracy of the measurements was estimated to be ±2 min. The critical distance is the measure of the smoke removal efficiency.

Figure 8:
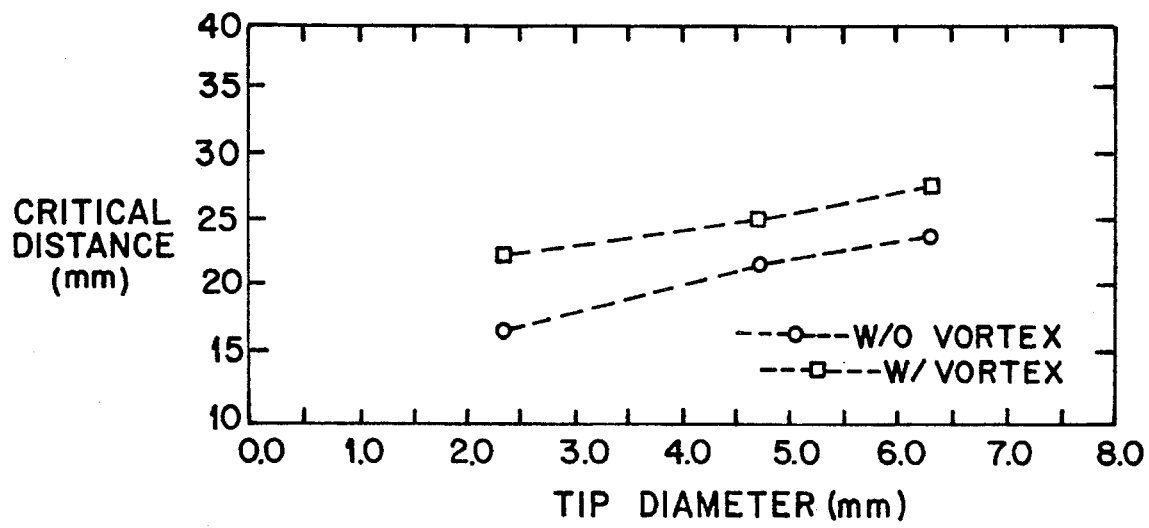
FIG. 8 is a graph of the results of the experiment conducted using the equipment of FIGS. 6 and 7.

All data is shown in Table 1 and illustrated in FIG. 8. The statistical results are in Table 2.

TABLE 1

Critical Distance Measurements with Different Orifice Sizes (distance that smoke is attracted into an orifice with a constant velocity).

| Type of Orifice | Tip Diameter (mm) | "out-to-in" critical dist. (mm) | Per-cent Improvement | "in-to-out" critical dist. (mm) | Per-cent Improvement |
|---|---|---|---|---|---|
| w/o vortex | 6.35 | 24.0 ± 0.7 | | 27.4 ± 0.05 | |
| with vortex | 6.35 | 27.6 ± 0.5 | 15.0 | 31.0 ± 1.0 | 13.1 |
| w/o vortex | 4.76 | 21.8 ± 0.5 | | 25.4 ± 0.9 | |
| with vortex | 4.76 | 25.0 ± 0.7 | 14.7 | 27.6 ± 1.1 | 8.7 |
| w/o vortex | 2.38 | 16.6 ± 0.5 | | 21.0 ± 0.7 | |
| with vortex | 2.38 | 22.2 ± 0.8 | 33.7 | 25.2 ± 0.4 | 20.0 |

Notes:
(1) The velocity (measured by a rotometer flowmeter) was 25 LPM for the orifices without drills, but dropped approximately 1 LPM (to 24) for the orifices with drills. This drop was attributed to the increase in resistance from the drill cross-section area. The flowmeter was adjusted back to 25 LPM so that the results would be comparable for both sets of data.
(2) The n = 5 for all data. All data reported as Mean ± 1 S.D.
(3) See previous discussion for the definition of "critical distance".

TABLE 2

Statistical Analysis Results (T-test)

| Data at Direction | Comparison Description | p value | Significant 0.95 ? |
|---|---|---|---|
| out-to-in (towards the orifice) | 6.35 mm - with vortex vs without vortex | 0.0010 | Yes |
| | 4.76 mm - with vortex vs. without vortex | 0.0012 | Yes |
| | 2.38 mm - with vortex vs. without vortex | 0.0010 | Yes |
| in-to-out (away from the orifice) | 6.35 mm - with vortex vs without vortex | 0.0011 | Yes |
| | 4.76 mm - with vortex vs. without vortex | 0.0213 | Yes |

TABLE 2-continued

Statistical Analysis Results (T-test)

| Data at Direction | Comparison Description | p value | Significant 0.95 ? |
|---|---|---|---|
| | 2.38 mm - with vortex vs. without vortex | 0.0010 | Yes |

The efficiency of smoke removal (=increased critical distance) was greatest with the largest orifice diameter. This is consistent with flow line theory which states that the area of the orifice is proportional to the amount of air that it can "attract". It is also consistent with resistance to flow physics (the larger the orifice diameter the less the resistance to that flow).

The efficiency of smoke removal was also larger with the vortex inserts in place (see Table 2 for p values). The spirals formed seem to enhance the flow lines and increase the drawing power. There is a high probability that machining a small radius on the sharp right angles of the orifice tips would also enhance the vacuum efficiency.

There is also a possibility that the area lost to the drill cross section actually skews the results. If the orifice size was to be redefined as "effective open area" rather than orifice diameter, then it would be correct to compare, for example, data from the 6.35 mm (with vortex) to the 4.76 mm (without vortex). If this hypothesis holds true, the rationale of using a vortex would become even more apparent.

Finally, during the testing it was noticed that the closer that the orifice (vacuum source) is to the smoke source, the greater the efficiency. This was intuitively clear and was substantiated by observations.

TEST 4

A fourth set of tests were performed which used the large diameter orifice (6.35 mm) from Test 3 but varied the turn density of the insert. It concluded that a spiral density of 2 turns/25 mm has greater efficiency than a spiral density of 1 turn/25 mm.

The objective of this experiment was to determine the smoke removal efficiency for the following tip configurations:

a) Vortex that has one (1) turn in 26 mm.
b) Vortex that has one and one-half (1 ½) turns in 25 mm.
c) Vortex that has two (2) turns in 25 mm.

In summary, it was demonstrated that increasing the turns on the vortex inducing insert showed significantly greater smoke removal. There was an 11.2% increase in efficiency when the turn density was increased from 1 turn to 2 turns per 25 mm.

The products used in this experiment are described below.

Three vortex turn densities were constructed out of brass stock (1¼" wide and e,fra 1/32"+ee thick) to fit inside an acrylic block (machined for Test 3 described previously) to a depth of 25 mm. The turns (per/25 mm) were one (1), one and one-half (1 ½) and two (2). All fit inside the 0.635 mm (¼") I.D. hole on the distal side of the acrylic block. The sides of the orifice tips were at sharp right angles. It was estimated that the spirals blocked approximately 3% of the orifice area (as compared to the approximately 40% blockage for the drill inserts—see Test 3).

Figure 10A:
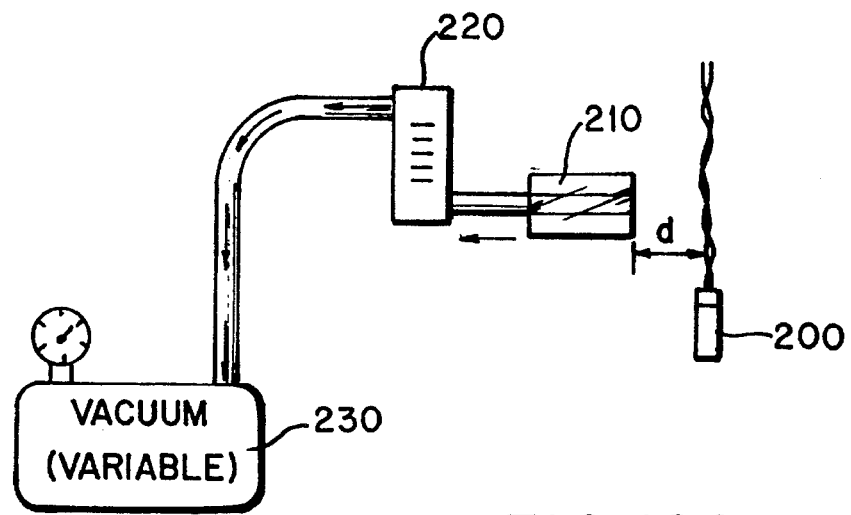
FIG. 10A shows an experiment arrangement including the location of distance "d", and orifice block and smoke source.

The circuit was set up per FIG. 10a. A vacuum was drawn through 6.35 mm (¼") tubing at a regulated 25 liters/minute gas flow rate. The distal end of the tubing was attached to the orifice and vacuum flow initiated.

The smoke source (filtered cigarettes) was placed 6 cm inferior to the orifice and moved towards the vacuum. If no vacuum was applied, the smoke rose in a concentrated stream for approximately 10–12 cm and then progressively dissipated. Care was taken to avoid any interfering movement of air. A total of five samples were recorded for each spiral.

Figure 10B:
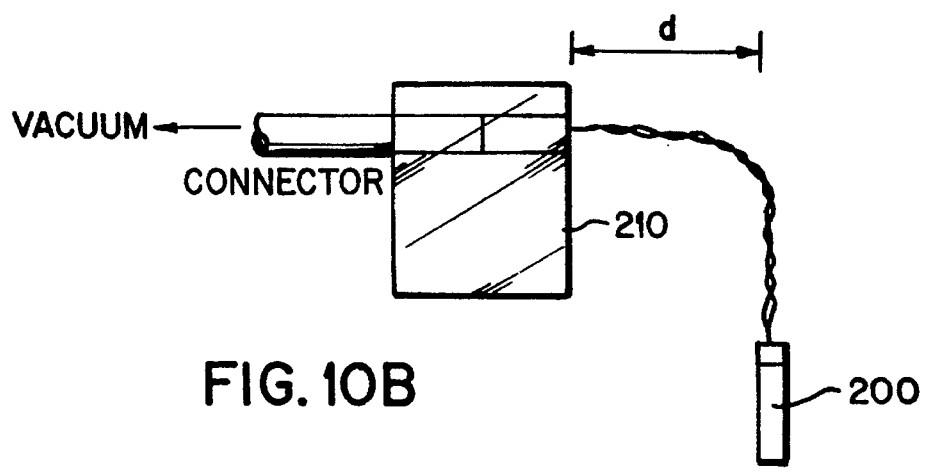
FIG. 10B is a detailed schematic view of the orifice block and smoke source with distance "d"

The "critical distance" was defined as the distance "d" (in mm) at which the entire (100%) smoke flow was drawn into the vacuum orifice at an obvious right angle to the non-vacuum rising flow (see FIG. 10b). The accuracy of the measurements was estimated to be ±2 mm.

The "starting distance" was defined as the distance "d"(in mm) at which any smoke flow was drawn into the vacuum orifice. The accuracy of these measurements was estimated to be ±3 mm.

Figure 9:
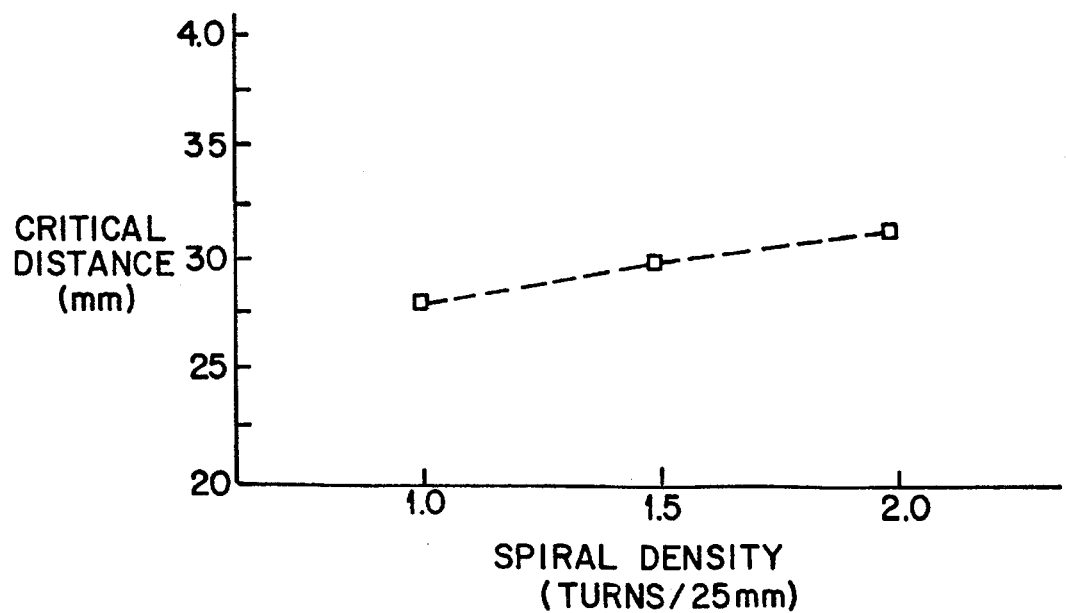
FIG. 9 shows a plot of critical distance measured against spiral density.

All data is shown in Table 3 and illustrated in FIG. 9. The statistical results are in Table 4.

The efficiency of smoke removal (=increased critical distance) was greatest with the most dense spiral (most turns/25 mm).

The critical distance was also greater for this "low cross-sectional" spiral as compared to the data obtained in Test 3 (the mean critical distance was 31.2 mm for the brass insert (2 turns) and 27.6 mm for the drill insert—a 13.0% improvement). The reproducibility of this data has not been substantiated at this time, however.

The difference between the critical distance and the starting distance did not become significantly greater or smaller with an increase in turn density.

TABLE 3

Critical Distance and Starting Distance Measurements with Different Turn Densities (6.35 mm diameter)

| Turn Density (/25 mm) density | Critical Distance (mm) | % Improvement over the previous spiral density | Starting Distance (mm) | % Improvement over the previous spiral |
| --- | --- | --- | --- | --- |
| 1 turn | 28.0 ± 0.7 | | 34.0 ± 0.7 | |
| 1½ turns | 29.8 ± 0.8 | 6.4 | 36.6 ± 0.5 | 7.6 |
| 2 turns | 31.2 ± 0.8 | 4.7 | 37.8 ± 0.8 | 3.3 |

Notes:
(1) The velocity (measured by a rotometer flowmeter) was 25 LPM. There was no detectable drop in velocity when the brass spirals were added.
(2) The n = 5 for all data. All data reported as Mean ± 1 S.D.
(3) See previous discussion for the definition of "critical distance" and "starting distance".

TABLE 4

Statistical Analysis Results (T-test)

| Comparison Description | p value | Significant at 0.95 ? |
| --- | --- | --- |
| 1 turn to 1½ turns | 0.0367 | Yes |
| 1 turn to 2 turns | 0.0054 | Yes |
| 1½ turns to 2 turns | 0.0046 | Yes |

TEST 5

A fifth set of tests were performed which compared three orifices of constant diameter (again 6.35 mm) and constant turn density (1 turn/25 mm), but of increasing spiral length. The results show that a longer (75 mm) length yields greater efficiency than a shorter length (25 mm).

The objective of this set of tests was to determine the smoke removal efficiency for the following brass spiral tip configurations:

a) Vortex that has one (1) turn in 25 mm and is 25 mm in length.
b) Vortex that has one (1) turn in 25 mm and is 50 mm in length.
c) Vortex that has one (1) turn in 25 mm and is 75 mm in length.

In summary, increasing the length of the vortex inducing insert showed significantly greater smoke removal. There was an 26.9% increase in efficiency when the length was increased from 25 mm to 75 mm.

Figure 11:
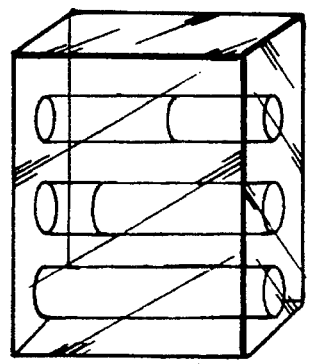
FIG. 11 is a block diagram of three orifice diameters used to demonstrate the efficiency of the vortex tube.

Three spiral lengths were constructed out of brass stock (¼" wide and ¹⁄₃₂" thick) to fit inside an acrylic block to a diameter of 6.35 mm (see FIG. 11). The turn density was one (1) per 25 mm. The lengths were 25, 50, and 75 mm. The sides of the orifice tips were at sharp right angles. It was estimated that the spirals blocked approximately 3% of the orifice area (as compared to the approximately 40% blockage for the drill inserts—Test 3).

The circuit was set up per FIG. 12a. A vacuum was drawn through 6.35 mm (¼") tubing at a regulated 26 liters/minute gas flow rate. The distal end of the tubing was attached to the orifice and vacuum flow initiated.

The smoke source (filtered cigarettes) was placed 6 cm inferior to the orifice and moved towards the vacuum. If no vacuum was applied, the smoke rose in a concentrated stream for approximately 10–12 cm and then progressively dissipated. Care was taken to avoid any interfering movement of air. A total of five samples were recorded for each spiral length.

The "critical distance" was defined as the distance "d" (in mm) at which the entire (100%) smoke flow was drawn into the vacuum orifice at an obvious right angle to the non-vacuum rising flow (see FIG. 12b). The accuracy of the measurements was estimated to be ±2 mm.

The "starting distance" was defined as the distance "d" (in mm) at which any smoke flow was drawn into the vacuum orifice. The accuracy of these measurements was estimated to be ±3 mm.

All data is shown in Table 5 and illustrated in FIG. 13. The statistical results are in Table 6.

The efficiency of smoke removal (=increased critical distance) was greatest with the longest spiral length.

The spiral distance was also greater for this "low cross-sectional" spiral as compared to the data obtained in Test 3.

The reproducability of this data seems to be quite good. If data from one (1) turn/25 mm density through a 6.35 mm diameter orifice of 25 mm spiral length is compared for the three tests done to date, results of 27.6 mm (Test 3), 28.0 mm (Test 4) and 29.0 mm (this test) are obtained.

TABLE 5

Critical Distance and Starting Distance Measurements with Increased Spiral Lengths (6.35 mm diameter).

| Spiral Length (mm) | Critical Distance (mm) | % Improvement over the previous spiral length | Starting Distance (mm) | % Improvement over the previous spiral length |
| --- | --- | --- | --- | --- |
| 25 | 29.0 ± 0.7 | | 34.4 ± 0.5 | |
| 50 | 31.0 ± 0.7 | 6.9 | 36.4 ± 0.5 | 5.8 |
| 75 | 36.8 ± 0.8 | 18.7 | 39.0 ± 0.7 | 7.1 |

TABLE 5-continued

Notes:
(1) The velocity (measured by a rotometer flowmeter) was 25 LPM. There was no detectable drop in velocity when the brass spirals were added.
(2) The n = 5 for all data. All data reported as Mean ± 1 S.D.?
(3) See text for the definition of "critical distance" and "starting distance".

TABLE 6

Statistical Analysis Results (T-test)

| Comparison Description | p value | Significant at 0.95 ? |
|---|---|---|
| 25 to 50 mm | 0.0217 | Yes |
| 50 to 75 mm | 0.001 | Yes |
| 25 to 75 mm | 0.001 | Yes |

The smoke removal device is discussed herein as being associated with an electrosurgical device such as a cauterizing pencil. However, it can clearly be used with any other smoke-generating surgical technique, such as coagulation or laser surgery. Moreover, it should be understood that the vortex smoke removal is adaptable for many other uses, such as smoke removal in restaurants, fire fighting and other industrial applications. For example, if a vortex creating member of the appropriate size were attached to the end of a large hose, the hose could be inserted into a burning building to remove the smoke at a faster rate, allowing fire fighters to enter the building without fear of collapsing from smoke inhalation. Additionally, if a vortex creating member were attached to a hose placed above a restaurant stove, the smoke could be cleared faster, allowing the chef to work safely and comfortably.

Additional constructions of the device according to the invention are illustrated in FIGS. 14–17. In FIGS. 14 and 15, another embodiment of the invention is illustrated which utilizes an externally fluted central electrode 300, the major longitudinal length portion of which is in the form of an externally fluted body 302, defining a maximum external diameter 304. The electrical conductor 18 which applies an electrical potential to the central electrode 302 can be connected to the proximal end of the electrode in any conventional manner or may be connected to an intermediate portion thereof, through a switch 19, at point 19' as shown. At the distal end, the electrode tapers as shown to provide a vortex tip 306. In FIG. 15, a mating cylindrical probe housing 308 is also shown which has an internal diameter of 304' which substantially corresponds to the maximum diameter 304 of the helical flutes, fins or vanes. The diameters 304 and 304' are selected such that the flute on the body 302 can be received within the cylindrical probe housing with little clearance, so that the radially outermost extremities of the flutes are substantially in contact or abuttment with the inner surface of the cylindrical housing, thereby preventing substances drawn into the device from by-passing the helical channels defined by the flutes or fins. At the proximal end 308a, the cylindrical housing 308 is connected to a vacuum hose 130 by means of suitable joining and sealing member 310. The distal end of the housing 308b is advantageously tapered as shown.

In FIG. 16, a variant form of the probe is illustrated in schematic. The probe, generally designated by the reference numeral 320, incorporates an internally fluted cylindrical probe housing. The proximal end 320a of the housing is in fluid flow communication with and joined to vacuum hose 130 by means of conventional and joining member 310. The distal end of the housing 320b is tapered to provide an opening 320c at a distal end which has a diameter smaller than the diameter of the housing. In the embodiment of FIG. 16, the flutes, vanes, or fins are in the form of internal spirals 322. As with the other embodiments, one or more flutes, vanes or fins may be provided. A metallic electrode 326 is attached to the probe housing 320 as shown and connected to a control console for application of electrical potential by means of electrical conductors 328. In this embodiment, since the spirals are formed on the internal surfaces of the cylindrical housing, a longitudinal axial bore or through opening 324 may be provided which extends the length of the housing. The electrical conductors 328 may extend through this axial bore 324 to reach the electrode 326. When a laser beam is utilized in place of an electrode, the axial bore 324 can also serve as an optical pathway for the laser beam.

Turning to FIG. 18, a typical application of the use of the present invention is illustrated. The reference numeral 330 represents an operating room (OR) in which there is provided an operating room table 332. Surgeons are typically positioned at 334 and a nurse might be positioned at 336. As is common in operating rooms, numerous facilities are available, including oxygen, a vacuum, and the like through wall-mounted ports. In this instance, the OR wall 338 is shown provided with a standard vacuum port 340 which is adapted to receive a standard connector 342which is universally used for accessing standard vacuum ports. Such standard connectors are well-known to those skilled in the art. By attaching the vacuum hose to the standard vacuum port 340, a vacuum is established within the vacuum hose and, therefore, at the probe 308.

In accordance with an important feature in the present invention, a vacuum booster 344 is provided for enhancing, on demand, the magnitude of the vacuum applied to the surgical probe 308. In the embodiment illustrated in FIG. 18, the vacuum booster 344 is shown positioned in-line with the vacuum hose 130 between the surgical probe 308 and the standard vacuum port 340. While it is also possible with the present invention to utilize a stand-alone vacuum unit of the type disclosed in U.S. Pat. Nos. 4,963,134 and 5,047,072, it is believed more advantageous to place the booster in line so that all hazardous gases and contaminants are exhausted to the standard vacuum port and not re-released into the operating room.

The vacuum booster 344 is shown connected to a console 346, which can also be the Bovie console typically used for surgical probes. However, this is not critical and a separate control can be used for the vacuum booster. The control console 346, therefore, includes a conductor 348 coupled to the vacuum booster 344 as well as an electrical conductor 18 which is conventionally used to power the surgical probe.

The sequences of operation and the levels of control of the surgical probe and the power booster may vary, and are not considered to be critical. A presently preferred embodiment, however, is illustrated in FIG. 19. Thus, a motor 350 which forms part of the vacuum booster 344 is shown connected by means of a double pole (352' and 352"), triple throw switch 352 to one of three different positions "a", "b" and "c". In position "a" of the switch 352', the booster motor 350 is left open and, therefore, inactive. In the embodiment of FIG. 18, therefore, the only vacuum in the vacuum hose 130 under those circumstances is the standard vacuum provided in the OR room at the port 340. The same is true when the switch 352' is moved to position "b". However, when the switch 352' is moved to position "c", the motor 350 is connected across a power source 356 which may be either a variable DC power supply, where the motor 350 and the DC motor, or to a variable transformer, where the motor 350 is an AC motor.

The second pole 352" of the switch 352 is likewise provided with three contacts. Where the switch 352" is in position "a" or position "c", a suitable signal is provided at conductor 354 which activates the Bovi unit in a conventional manner and energizes the probe 308. However, when the switch 352" is in position "b", no signal is applied at the conductor 354 and the probe remains de-energized. It will be appreciated, therefore, that if the switches 352' and 352" are mechanically coupled or ganged together, and the positions "b" are the normal positions of the switch 19, the vacuum booster 344 and the probe are normally de-energized. If the surgeon wants to energize the probe but does not want to initiate the vacuum booster, the switch can be rocked to position "a", in which case, as described, only the standard vacuum will be available at the probe. However, when additional suction is needed, the switch can be rocked into position "c" in which case both the probe as well as the vacuum booster are energized at a level selected by an adjustment of the power source 356. In this way, the surgeon has greater control over the evacuation of gases, noxious odors and other contaminents.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A device for removing smoke from the air proximate to a smoke generator, comprising a generally elongate hollow tubular housing having entrance and exit open ends; vortex means at least at said entrance end of said tubular housing, first suction means, said exit end of said tubular housing including means for being connected to said first suction means for creating an air suction within said tubular housing and at said entrance end proximate to the smoke generator, said, first suction means and said vortex means cooperating to create a vortex flow of air and smoke at said entrance end of said housing; and second suction means connected to said tubular housing for selectively increasing the suction and the vortex flow at said entrance end of said tubular housing to thereby enhance the vortex and air suction at said entrance end to draw in and remove smoke formed by the smoke generator.

2. The device of claim 1, wherein said vortex means is a helical member extending substantially along the entire axial length of said tubular housing.

3. The device of claim 1, wherein said vortex means is a helical member forming at least one opening with an inside surface of the tubular housing through which the smoke enters at the entrance end of said tubular housing.

4. A device of claim 1, in combination with a smoke generator which comprises an electrosurgical device which includes an electrode which forms a cutting blade, and said vortex means is provided concentrically around said electrode of the electrosurgical device, said electrode protruding beyond an end of said vortex means.

5. A device of claim 1, wherein said second suction means comprises an auxiliary vacuum booster connected in-line between said tubular housing and said first suction means.

6. A device of claim 1, further comprising control means for controlling the magnitude of suction provided by said second suction means.

7. A device of claim 1, wherein said tubular housing includes control means for operating the device and said second suction means.

8. A device of claim 1, wherein said vortex means comprise internal flutes provided on an internal surface of said tubular housing.

9. A device of claim 8, wherein an electrode is mounted on said tubular housing to project beyond a distal end thereof.

10. A device of claim 1, wherein said vortex means comprises an externally fluted central electrode having a maximum diameter substantially equal to an inner diameter of said tubular housing and having a tapered distal end which extends beyond said tubular housing to form a tip electrode.

* * * * *